US011305056B2

(12) United States Patent
Mojarrad et al.

(10) Patent No.: US 11,305,056 B2
(45) Date of Patent: Apr. 19, 2022

(54) NEEDLE INSERTION-RETRACTION SYSTEM HAVING DUAL TORSION SPRING SYSTEM

(71) Applicant: AMGEN INC., Thousand Oaks, CA (US)

(72) Inventors: Mehran Mojarrad, Thousand Oaks, CA (US); Scott Robert Gibson, Granada Hills, CA (US); Adam Livingston, Oceanside, CA (US)

(73) Assignee: AMGEN INC., Thousand Oaks, CA (US)

( * ) Notice: Subject to any disclaimer, the term of this patent is extended or adjusted under 35 U.S.C. 154(b) by 274 days.

(21) Appl. No.: 16/620,016

(22) PCT Filed: Jul. 14, 2018

(86) PCT No.: PCT/US2018/040671
§ 371 (c)(1),
(2) Date: Dec. 6, 2019

(87) PCT Pub. No.: WO2019/014014
PCT Pub. Date: Jan. 17, 2019

(65) Prior Publication Data
US 2020/0230313 A1    Jul. 23, 2020

Related U.S. Application Data

(60) Provisional application No. 62/532,868, filed on Jul. 14, 2017.

(51) Int. Cl.
*A61M 5/142*    (2006.01)
*A61M 5/145*    (2006.01)

(52) U.S. Cl.
CPC ... *A61M 5/142* (2013.01); *A61M 2005/14256* (2013.01); *A61M 2005/14506* (2013.01)

(58) Field of Classification Search
CPC .......... A61M 5/14244; A61M 5/14248; A61M 2005/14252; A61M 5/14;
(Continued)

(56) References Cited

U.S. PATENT DOCUMENTS

| 1,471,091 A | 10/1923 | Bessesen |
| 3,115,133 A | 12/1963 | Morando |

(Continued)

FOREIGN PATENT DOCUMENTS

| EP | 2667913 A2 | 12/2013 |
| WO | WO-2012103428 A2 | 8/2012 |

(Continued)

OTHER PUBLICATIONS

Written Opinion of the International Searching Authority for PCT International Application No. PCT/US2018/040671, dated Sep. 20, 2018.

(Continued)

*Primary Examiner* — Jason E Flick
(74) *Attorney, Agent, or Firm* — Marshall, Gerstein & Borun LLP

(57) ABSTRACT

An insertion/retraction mechanism for a drug delivery device is disclosed. The insertion/retraction mechanism includes a retraction hub, an insertion hub, an insertion/retraction mechanism housing, and a dual torsion spring system. The retraction hub includes a first primary rotational stop and a second primary rotational stop extending radially inwardly from an inside surface. The insertion hub is disposed inside the retraction hub and comprises a first complementary rotational stop and a second complementary rotational stop extending radially outwardly from an outside surface. The dual torsion spring system causes the first primary rotational stop and the second primary rotational stop to selectively engage the first complementary rotational (Continued)

stop and the secondary rotational stop, respectively, and further causes the retraction hub to rotate relative to the insertion/retraction mechanism housing as the insertion/retraction mechanism moves between an initial position, an inserted position, and a retracted position.

20 Claims, 5 Drawing Sheets

(58) Field of Classification Search
CPC ......... A61M 2005/14256; A61M 2005/14506; A61M 5/142; A61M 5/145
See application file for complete search history.

(56) References Cited

U.S. PATENT DOCUMENTS

| | | | |
|---|---|---|---|
| 3,207,157 A | 9/1965 | Murdoch | |
| 3,892,237 A | 7/1975 | Steiner | |
| 4,758,226 A | 7/1988 | Carre | |
| 4,790,824 A | 12/1988 | Morrow et al. | |
| 4,861,335 A | 8/1989 | Reynolds | |
| 4,926,860 A | 5/1990 | Stice et al. | |
| 5,300,030 A | 4/1994 | Crossman et al. | |
| 5,437,640 A | 8/1995 | Schwab | |
| 5,840,061 A | 11/1998 | Menne et al. | |
| 6,299,601 B1 | 10/2001 | Hjertman | |
| 6,387,078 B1 | 5/2002 | Gillespie, III | |
| 6,589,210 B1 | 7/2003 | Rolfe | |
| 6,605,067 B1 | 8/2003 | Larsen | |
| 7,530,964 B2 | 5/2009 | Lavi et al. | |
| 7,654,983 B2 | 2/2010 | De La Serna et al. | |
| 7,736,333 B2 | 6/2010 | Gillespie, III | |
| 7,846,132 B2 | 12/2010 | Gravesen et al. | |
| 8,002,753 B2 | 8/2011 | Krumme et al. | |
| 8,357,120 B2 | 1/2013 | Moller et al. | |
| 8,684,969 B2 | 4/2014 | Moller et al. | |
| 8,715,236 B2 | 5/2014 | Barrelli et al. | |
| 8,734,394 B2 | 5/2014 | Adams et al. | |
| 8,758,304 B2 | 6/2014 | Kemp et al. | |
| 8,784,363 B2 | 7/2014 | Frederickson et al. | |
| 8,808,244 B2 | 8/2014 | Adlon et al. | |
| 8,808,250 B2 | 8/2014 | Ekman et al. | |
| 8,998,851 B2 | 4/2015 | Constantineau et al. | |
| 9,119,920 B2 | 9/2015 | Cowe | |
| 9,132,242 B2 | 9/2015 | Kemp et al. | |
| 9,227,016 B2 | 1/2016 | Ekman et al. | |
| 9,242,044 B2 | 1/2016 | Markussen | |
| 9,327,080 B2 | 5/2016 | Boettger et al. | |
| 9,421,336 B2 | 8/2016 | Ekman et al. | |
| 9,427,525 B2 | 8/2016 | Barrow-Williams et al. | |
| 9,457,149 B2 | 10/2016 | Kemp et al. | |
| 9,533,106 B2 | 1/2017 | Hansen et al. | |
| 9,572,937 B2 | 2/2017 | Ekman et al. | |
| 2002/0095120 A1 | 7/2002 | Larsen et al. | |
| 2006/0287630 A1 | 12/2006 | Hommann | |
| 2007/0293787 A1 | 12/2007 | Taylor et al. | |
| 2012/0029385 A1* | 2/2012 | Chong | A61M 5/14248 600/583 |
| 2013/0123710 A1 | 5/2013 | Ekman et al. | |
| 2013/0218128 A1 | 8/2013 | Cowe | |
| 2013/0289525 A1 | 10/2013 | Kemp et al. | |
| 2014/0088508 A1 | 3/2014 | Ryan et al. | |
| 2014/0303563 A1 | 10/2014 | Moeller et al. | |
| 2015/0141929 A1 | 5/2015 | Fabien et al. | |
| 2015/0306307 A1* | 10/2015 | Cole | A61M 5/158 604/508 |
| 2016/0038678 A1 | 2/2016 | Kemp et al. | |
| 2016/0129188 A1 | 5/2016 | Kiilerich | |
| 2016/0213837 A1* | 7/2016 | Schabbach | A61M 5/14244 |
| 2016/0250417 A1 | 9/2016 | Olson | |
| 2019/0160230 A1* | 5/2019 | Yudelevich | A61M 5/322 |

FOREIGN PATENT DOCUMENTS

| | | |
|---|---|---|
| WO | WO-2016001298 A1 | 1/2016 |
| WO | WO-2016001299 A1 | 1/2016 |
| WO | WO-2016041883 A1 | 3/2016 |
| WO | WO-2016130679 A2 | 8/2016 |

OTHER PUBLICATIONS

International Search Report for PCT International Application No. PCT/US2018/040671, dated Sep. 20, 2018.
"Model Study of the Pressure Build-Up During Subcutaneous Injection", M. Thomsen et al., Aug. 8, 2014, http://journals.plos.org/plosone/article?id=10.1371/journal.pone.0104054.
"Strength Based Design of Compression Springs for Auto-Injector Syringes", S. Shaik et al., May 31, 2016, http://ijesc.org/upload/356eeed335352c862dd86e71d5713d15.Strength%20Based%20Design%20of%20Compression%20Springs%20for%20Auto-Injector%20Syringes.pdf.

* cited by examiner

NEEDLE INSERTION-RETRACTION SYSTEM HAVING DUAL TORSION SPRING SYSTEM

CROSS-REFERENCE TO RELATED APPLICATION

This is the United States National Phase of PCT/US2018/040671, filed Jul. 3, 2018, which claims the priority benefit of U.S. Provisional Patent Application No. 62/532,868, filed Jul. 14, 2017, the entire contents of each of which are hereby incorporated herein by reference.

FIELD OF DISCLOSURE

The present disclosure generally relates to drug delivery devices and more particularly, but not necessarily exclusively, to inserting and retracting a flexible needle using a dual torsion spring system in conjunction with an insertion hub and a retraction hub.

BACKGROUND

Some drug delivery devices, such as on-body injectors, may be temporarily attached to a patient to deliver a drug via an injection needle or some other means over an extended period of time. The drug delivery device may be attached to the tissue of the patient's abdomen, thigh, arm, or some other portion of the patient's body.

In some cases, the drug delivery device may be worn by the patient for several minutes or hours while the drug is injected. For example, viscous drugs, including some biologics, can have long injection times due to the force needed to expel them from the drug delivery device. Furthermore, some drug delivery devices are configured to be attached to the patient at a doctor's office, and then later deliver the drug to the patient when the patient returns to his or her home. For these reasons and others, a rigid injection member may be left inside the patient for a substantial amount of time, which can result in patient discomfort or unease.

In addition, some existing drug delivery devices use external features for needle safety, requiring the patient to remove the drug delivery device while a rigid needle is still inside the patient. Depending upon the angle, depth, and stiffness of the needle, this can cause patient discomfort and the anxiety of seeing the needle afterward.

As a result, insertion/retraction mechanisms have been disposed within drug delivery devices to accomplish insertion and/or retraction movements of the needle in manners that reduce the burden on the patient and minimize chance of error during application of the drug delivery devices. Such an insertion/retraction mechanism, however, may increase the overall size, complexity, and/or cost of the drug delivery device.

SUMMARY

In accordance with a first aspect, a drug delivery device includes a main housing having a container, a fluid pathway connector coupled to the container, a pressure supply device, and an insertion/retraction mechanism including a retraction hub, an insertion hub, and a dual torsion spring system. The insertion/retraction mechanism is disposed within the main housing and operatively coupled to the pressure supply device. The fluid pathway connector defines a fluid flow path between the container and the insertion/retraction mechanism. The retraction hub comprises an inside surface, a first primary rotational stop extending radially inwardly from the inside surface, and a second primary rotational stop extending radially inwardly from the inside surface. The insertion hub is disposed inside of the retraction hub and comprises a shaft having an outside surface, a first complementary rotational stop extending radially outwardly from the outside surface, and a second complementary rotational stop extending radially outwardly from the outside surface. The insertion hub further comprises a spindle connected to the shaft. The spindle has a needle pathway. The insertion/retraction mechanism includes an insertion/retraction mechanism housing that houses the retraction hub and the insertion hub in a rotatable manner and comprises a needle exit aperture. A flexible needle is connected to the fluid flow path and is configured to extend through the needle pathway of the spindle of the insertion hub and to selectively pass through the needle exit aperture of the insertion/retraction mechanism housing during insertion and retraction of the flexible needle. The dual torsion spring system includes a right wound torsion spring and a left wound torsion spring. The dual torsion spring system is operably connected to the retraction hub, the insertion hub, and the insertion/retraction mechanism housing. An activation trigger is operably connected to the dual torsion spring system.

In accordance with the first aspect, in an initial position, the first primary rotational stop engages the first complementary rotational stop, the retraction hub is in a first rotational position relative to the insertion/retraction mechanism housing, and the flexible needle does not pass through the needle exit aperture. In an inserted position, the second primary rotational stop engages the second complementary rotational stop as a result of the insertion hub being rotated relative to the retraction hub by a first spring bias provided by the dual torsion spring system. In the inserted position, the retraction hub is in the first rotational position relative to the insertion/retraction mechanism housing, and the flexible needle passes through the needle exit aperture. In a retracted position, the second primary rotational stop engages the second complementary rotational stop, the retraction hub is in a second rotational position relative to the insertion/retraction mechanism housing as a result of the retraction hub being rotated relative to the insertion/retraction mechanism housing by a second spring bias provided by the dual torsion spring system, and the flexible needle does not pass through the needle exit aperture.

In accordance with a second aspect, an insertion/retraction mechanism for a drug delivery device includes a retraction hub, an insertion hub, and a dual torsion spring system. The retraction hub comprises an inside surface, a first primary rotational stop extending radially inwardly from the inside surface, and a second primary rotational stop extending radially inwardly from the inside surface. The insertion hub is disposed inside of the retraction hub and comprises a shaft having an outside surface, a first complementary rotational stop extending radially outwardly from the outside surface, and a second complementary rotational stop extending radially outwardly from the outside surface. The insertion hub further comprises a spindle connected to the shaft. The spindle has a needle pathway. The insertion/retraction mechanism includes an insertion/retraction mechanism housing that houses the retraction hub and the insertion hub in a rotatable manner and comprises a needle exit aperture. A flexible needle is configured to extend through the needle pathway of the spindle of the insertion hub and to selectively pass through the needle exit aperture of the insertion/retraction mechanism housing during insertion and retraction of the flexible needle. The dual torsion spring system includes a right wound torsion spring and a left wound torsion spring. The dual torsion spring system is operably connected to the retraction hub, the insertion hub, and the insertion/retraction mechanism housing. An activation trigger is operably connected to the dual torsion spring system.

In accordance with the second aspect, in an initial position, the first primary rotational stop engages the first complementary rotational stop, the retraction hub is in a first rotational position relative to the insertion/retraction mechanism housing, and the flexible needle does not pass through the needle exit aperture. In an inserted position, the second primary rotational stop engages the second complementary rotational stop as a result of the insertion hub being rotated relative to the retraction hub by a first spring bias provided by the dual torsion spring system. In the inserted position, the retraction hub is in the first rotational position relative to the insertion/retraction mechanism housing, and the flexible needle passes through the needle exit aperture. In a retracted position, the second primary rotational stop engages the second complementary rotational stop, the retraction hub is in a second rotational position relative to the insertion/retraction mechanism housing as a result of the retraction hub being rotated relative to the insertion/retraction mechanism housing by a second spring bias provided by the dual torsion spring system, and the flexible needle does not pass through the needle exit aperture.

In accordance with a third aspect, a method of deploying a needle of an insertion/retraction mechanism from a drug delivery device comprises engaging a first primary rotational stop of a retraction hub with a first complementary rotational stop of an insertion hub in an initial position, triggering an activation trigger operably connected to a dual torsion spring to engage a second primary rotational stop of the retraction hub with a second complementary rotational stop of the insertion hub in an inserted position, and triggering the activation trigger to rotate the retraction hub relative to the insertion/retraction mechanism housing to achieve a retracted position. In the initial position, a flexible needle of the insertion/retraction mechanism is contained within the insertion/retraction mechanism housing and the retraction hub is placed in a first rotational position relative to the insertion/retraction mechanism housing. During triggering of the activation trigger operably connected to a dual torsion spring to engage a second primary rotational stop of the retraction hub with a second complementary rotational stop of the insertion hub in an inserted position, the dual torsion spring causes one of a right wound torsion spring and a left wound torsion spring of the dual torsion spring system to rotate the insertion hub relative to the retraction hub to achieve an inserted position. In the inserted position, the retraction hub is in the first rotational position relative to the insertion/retraction mechanism housing, and the flexible needle extends outside the insertion/retraction mechanism housing. During triggering the activation trigger to rotate the retraction hub relative to the insertion/retraction mechanism housing to achieve a retracted position, the other of the right wound torsion spring and the left wound torsion spring of the dual torsion spring system causes the retraction hub to rotate relative to the insertion/retraction mechanism housing. In the retracted position, the second primary rotational stop of the retraction hub engages the second complementary rotational stop of the insertion hub, the retraction hub is in a second rotational position relative to the insertion/retraction mechanism housing, and the flexible needle is contained within the insertion/retraction mechanism housing.

In further accordance with any one or more of the foregoing first and second aspects and method, the insertion mechanism for a drug delivery device and method may include any one or more of the following forms or method steps.

In one form, the retraction hub may further comprise a third primary rotational stop extending radially inwardly from the inside surface and a fourth primary rotational stop extending radially inwardly from the inside surface. The insertion/retraction mechanism housing may comprise a third complementary rotational stop and a fourth complementary rotational stop. The third primary rotational stop of the shaft of the insertion hub may engage the third complementary rotational stop of the insertion/retraction mechanism housing in the inserted position. The fourth primary rotational stop of the shaft of the insertion hub may engage the fourth complementary rotational stop of the insertion/retraction mechanism housing in the retracted position.

In another form, a distance that the flexible needle extends beyond the needle exit aperture in the inserted position may be determined by a diameter of the insertion hub and the first spring bias.

In yet another form, the right wound torsion spring and the left wound torsion spring may be integrated together into a single two-stage torsion spring.

In yet another form, the retraction hub may comprise an outside surface and preload notches extending radially outwardly from the outside surface. One of the right wound torsion spring and the left wound torsion spring may surround the outside surface of the retraction hub distal to the preload notches of the retraction hub and the other of the right wound torsion spring and the left wound torsion spring may surround the outside surface of the retraction hub proximal to the preload notches of the retraction hub.

In yet another form, the retraction hub may comprise an outside surface and a sliding rod notch extending radially outwardly from the outside surface. The insertion hub may comprise a sliding rod notch extending radially outwardly from the outside surface. The activation trigger may comprise a sliding rod axially aligned with the retraction hub and having an outside surface of varying outer diameter in contact with the sliding rod notch of the retraction hub and the sliding rod notch of the insertion hub. A first axial movement of the sliding rod may release the sliding rod from the sliding rod notch of the insertion hub, allowing one of the right wound torsion spring and the left wound torsion spring to rotate the insertion hub relative to the retraction hub to achieve the inserted position. A second axial movement of the sliding rod may release the sliding rod from the sliding rod notch of the retraction hub, allowing the other of the right wound torsion spring and the left wound torsion spring to rotate the retraction hub relative to the insertion/retraction mechanism housing in order to achieve the retracted position.

In yet another form, the activation trigger may include an insertion trigger selectively securing the insertion hub in place and a retraction trigger selectively securing the retraction hub in place. In the initial position, the insertion trigger may secure the insertion hub in place and the retraction trigger may secures the retraction hub in place. In the inserted position, the insertion trigger may not secure the insertion hub in place and the retraction trigger may secure the retraction hub in place. In the retracted position, the insertion trigger may not secure the insertion hub in place and the retraction trigger may not secure the retraction hub in place.

In yet another form, the activation trigger may comprise a first sliding trigger selectively securing one of the retraction hub or the insertion hub in place, a second sliding trigger selectively securing the other of the retraction hub or the insertion hub in place, a first muscle wire connected to the first sliding trigger, and a second muscle wire connected to the second sliding trigger. Electrical activation of the first muscle wire may cause the first muscle wire to contract, moving the first sliding trigger and thereby releasing the one of the retraction hub or the insertion hub, in order to allow one of the right wound torsion spring and the left wound torsion spring to rotate the insertion hub relative to the retraction hub to achieve the inserted position. Electrical activation of the second muscle wire may cause the second muscle wire to contract, moving the second sliding trigger and thereby releasing the other of the retraction hub or the insertion hub, in order to allow the other of the right wound torsion spring and the left wound torsion spring to rotate the retraction hub relative to the insertion/retraction mechanism housing in order to achieve the retracted position.

In one form of the method, triggering the activation trigger to achieve an inserted position may include moving an insertion trigger of the activation trigger so that the insertion trigger is not in contact with the insertion hub while a retraction trigger of the activation trigger is in contact with the retraction hub, and triggering the activation trigger to achieve a retracted position may include moving the retraction trigger so that the reaction trigger is not in contact with the retraction hub.

In another form of the method, triggering the activation trigger to achieve an inserted position may include a first axial movement of a sliding rod axially aligned with a retraction hub and an insertion hub and having an outside surface of varying outer diameter in contact with a sliding rod notch of the retraction hub and a sliding rod notch of the insertion hub, and triggering the activation trigger to achieve a retracted position may include a second axial movement of the sliding rod.

In yet another form of the method, triggering the activation trigger to achieve an inserted position may include electrical activation of a first muscle wire connected to a first sliding trigger selectively securing one of the retraction hub or the insertion hub in place, thereby causing the first muscle wire to contract, moving the first sliding trigger, and releasing the one of the retraction hub or the insertion hub. Triggering the activation trigger to achieve a retracted position may include electrical activation of a second muscle wire connected to a second sliding trigger selectively securing the other of the retraction hub or the insertion hub in place, thereby causing the second muscle wire to contract, moving the second sliding trigger, and releasing the other of the retraction hub or the insertion hub.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings are necessarily to scale.

DETAILED DESCRIPTION

Figures 1, 2A:
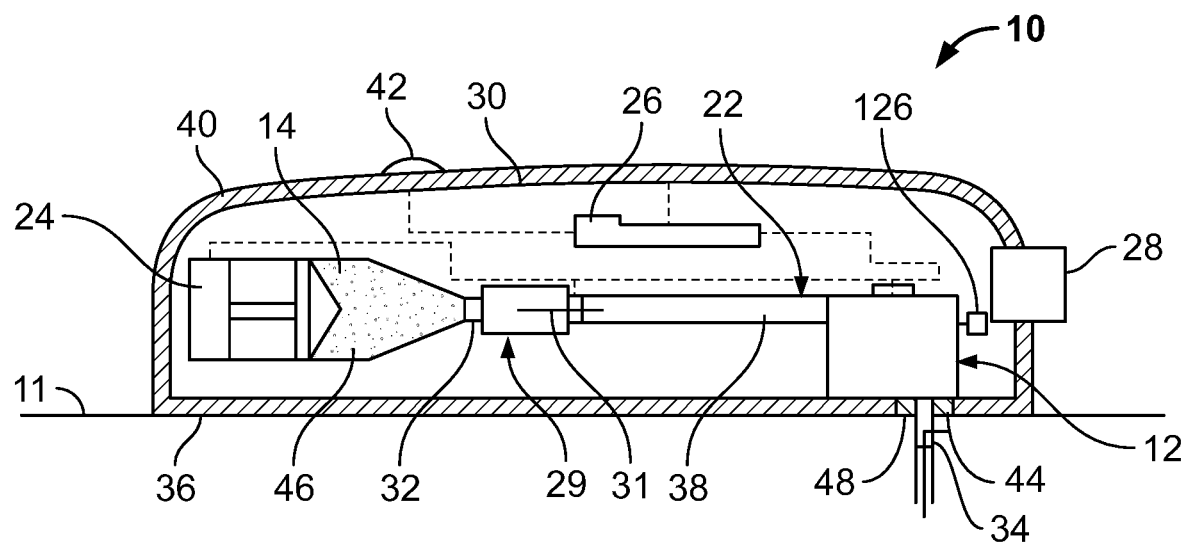
FIG. 1 is a schematic representation of an arrangement of a drug delivery device having an insertion/retraction mechanism in accordance with teachings of the present disclosure.
FIG. 2A is a perspective view of an arrangement of an insertion/retraction mechanism in an initial position having a mechanical activation trigger including a sliding rod in accordance with teachings of the present disclosure.

Referring to FIG. 1, a wearable drug delivery device 10 having an insertion/retraction mechanism 12 according to the present disclosure is depicted. In at least one example, the drug delivery device 10 may be configured as a wearable drug delivery device, such as an on-body injector, that may be attached to a patient's tissue 11 (e.g., the patient's skin) to administer delivery of a drug treatment. The drug delivery device 10 may automatically deliver a subcutaneous injection of a fixed or a patient/operator-settable dose of a drug over a controlled or selected period of time. The drug delivery device 10 may be intended for self-administration by the patient, but may also be used by a caregiver or a formally trained healthcare provider to administer an injection.

The drug delivery device 10 may include a container 14 coupled to the insertion/retraction mechanism 12 by a fluid pathway connector 22, a drive mechanism 24, and a controller 26, each of which may be disposed in a main housing 30 of the drug delivery device 10. An actuator 28 (e.g., a depressible button) may be arranged on an exterior of the main housing 30 and configured to initiate operation of the drug delivery device 10 by activating the insertion/retraction mechanism 12, the drive mechanism 24, and/or the controller 26 via mechanical and/or electrical means (shown in dotted lines in FIG. 1). The fluid pathway connector 22 defines a sterile fluid flow path 38 between the container 14 and the insertion/retraction mechanism 12. The fluid pathway connector 22 may include a container access mechanism 29 configured to insert a container needle 31 through a septum 32 associated with the container 14 to establish fluid communication between the container 14 and the sterile fluid flow path 38 in response to activation of the drug delivery device 10, for example, via the actuator 28. The main housing 30 may include a bottom wall 36 to be releasably attached (e.g., adhered with an adhesive) to the patient's skin 11, and a top wall 40 including one or more indicator lights 42 and/or a window (not illustrated) for viewing the container 14. An opening 44 may be formed in the bottom wall 36, and optionally a septum 48 may extend across the opening 44 to seal the interior of the main housing 30 prior to use. The exterior of the insertion/retraction mechanism 12 may be defined by an insertion/retraction mechanism housing separate from the main housing 30, as explained more below relative to each example insertion/retraction mechanism.

Generally, upon activation of the drug delivery device 10, the insertion/retraction mechanism 12 may insert a flexible needle 34 into the patient 12. The flexible needle may be made of a super-elastic material such as nitinol, a polymer, or another material that allows the needle to follow a curved path without sustaining damage. Simultaneously or subsequently, the drug delivery device 10 may enable, connect, or open necessary connections to establish fluid communication between the container 14 and the fluid pathway connector 22. Next, the drive mechanism 24 may force a drug 46 stored in the container 14 through the sterile fluid flow path 38 of the fluid pathway connector 22 and into the insertion/retraction mechanism 12 for subcutaneous delivery to the patient.

Figure 2B:
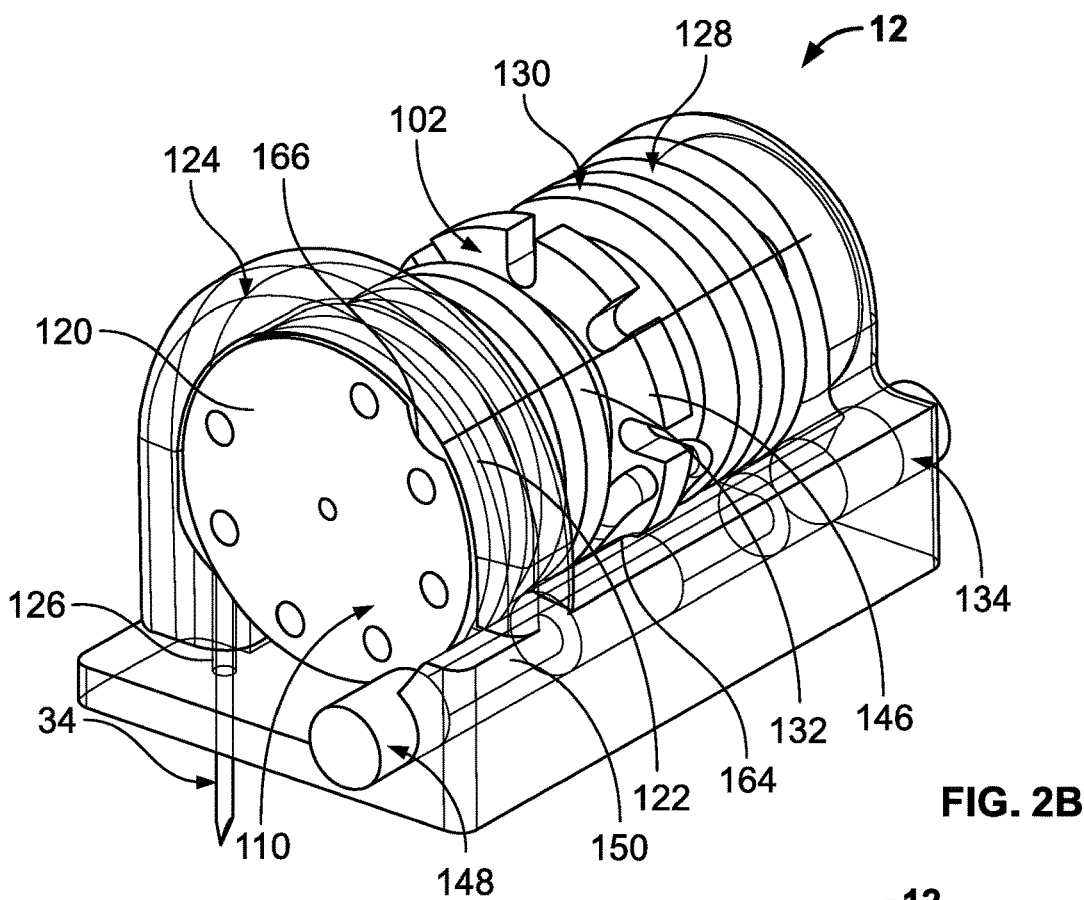
FIG. 2B is a perspective view of the embodiment of the insertion/retraction mechanism depicted in FIG. 2A in an inserted position.
Figure 2C:
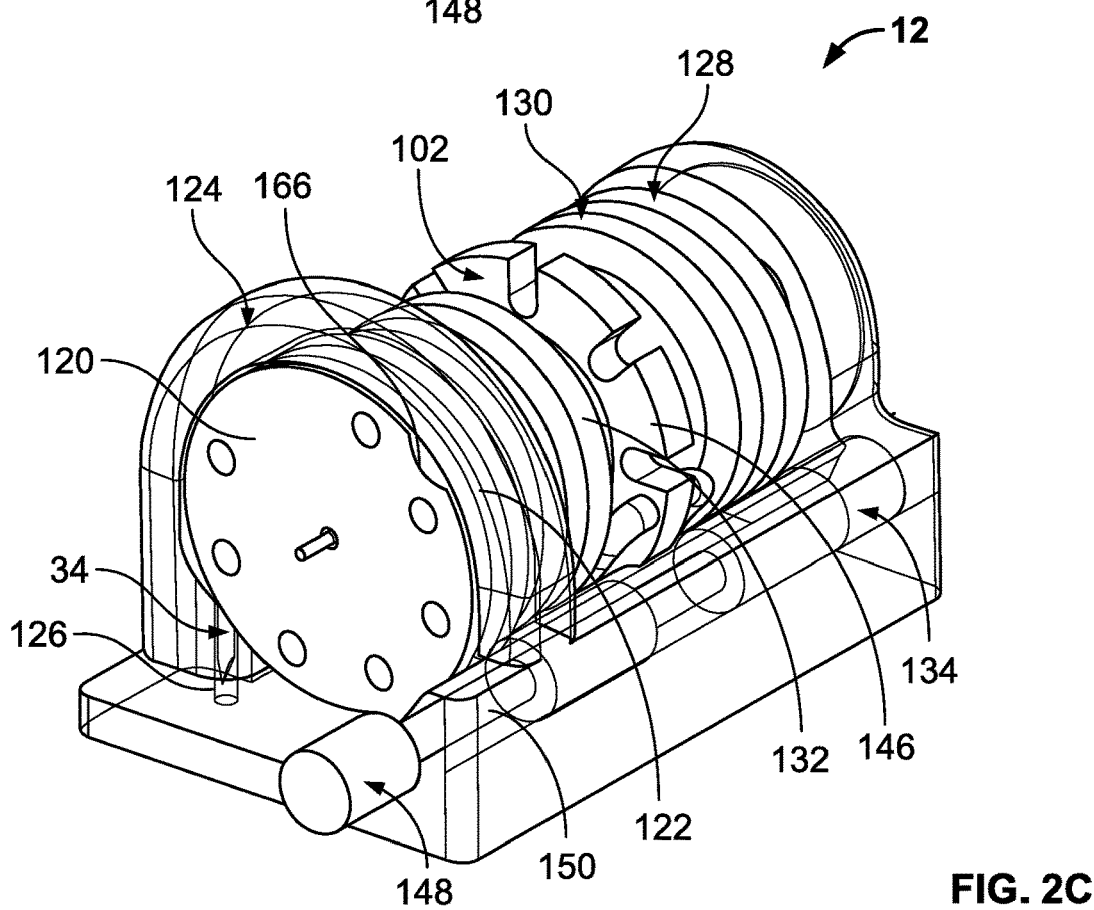
FIG. 2C is a perspective view of the embodiment of the insertion/retraction mechanism depicted in FIGS. 2A and 2B in a retracted position.

Turning to FIGS. 2A-2C, the insertion/retraction mechanism 12 of the drug delivery device 10 is shown in greater detail. Although configured for use with the drug delivery device 10 depicted in FIG. 1, the insertion/retraction mechanism 12 is a separate component that is compatible with a variety of drug delivery devices not herein described. The insertion/retraction mechanism 12 includes a retraction hub 102, an insertion hub 110 having a spindle 120 including a needle pathway 122, and an insertion/retraction mechanism housing 124 that houses the retraction hub 102 and the insertion hub 110 in a rotatable manner and comprises a needle exit aperture 126. The flexible needle 34 is provided within the insertion/retraction mechanism 12, is connected to the fluid flow path (not depicted), and is configured to extend through the needle pathway 122 of the spindle 120 of the insertion hub 110 and to selectively pass through the needle exit aperture 126 of the insertion/retraction mechanism housing 124 during insertion and retraction of the flexible needle 34. The ability of the flexible needle 34 to bend up to 360 degrees around a curved structure such as the spindle 120 allows for compact design and packaging of the insertion/retraction mechanism 12.

The insertion/retraction mechanism 12 includes a dual torsion spring system 128, which comprises a right wound torsion spring 130 and a left wound torsion spring 132. In some arrangements, the right wound torsion spring 130 and the left wound torsion spring 132 are integrated together into a single two-stage torsion spring. A single two-stage torsion spring offers the benefit of simplicity, part count reduction, and reduced cost in manufacture. In some arrangements, the retraction hub 102 comprises an outside surface 144 and preload notches 146 extend radially outwardly from the outside surface (shown in FIGS. 3A-3C), and (as shown in FIGS. 2A-2C) one of the right wound torsion spring 130 and the left wound torsion spring 132 surrounds the outside surface 144 of the retraction hub 102 distal to the preload notches 146 of the retraction hub 102 and the other of the right wound torsion spring 130 and the left wound torsion spring 132 surrounds the outside surface 144 of the retraction hub 102 proximal to the preload notches 146 of the retraction hub 102. The preload on the right wound torsion spring 130 and/or the left wound torsion spring 132 can be changed depending on which of the preload notches 146 the right wound torsion spring 130 and/or the left wound torsion spring 132 are connected. The dual torsion spring system 128 is operably connected to the retraction hub 102, the insertion hub 110, and the insertion/retraction mechanism housing 124. An activation trigger 134 is operably connected to the dual torsion spring system.

Figure 3A:
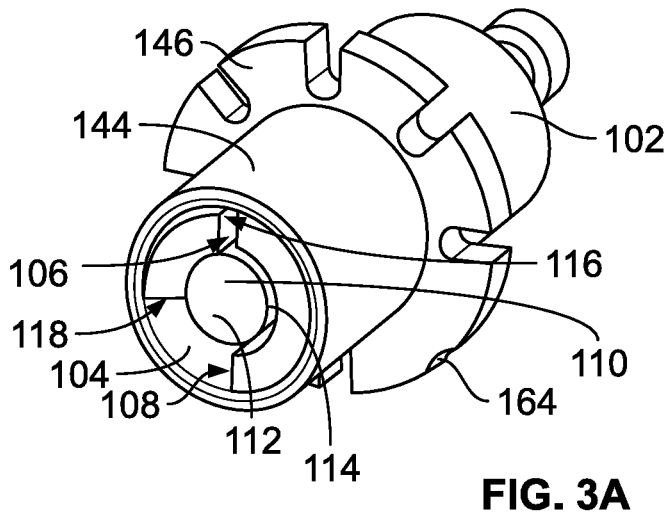
FIG. 3A is a perspective view of the insertion hub and retraction hub depicted in FIGS. 2A-2C in an initial position.
Figure 3B:
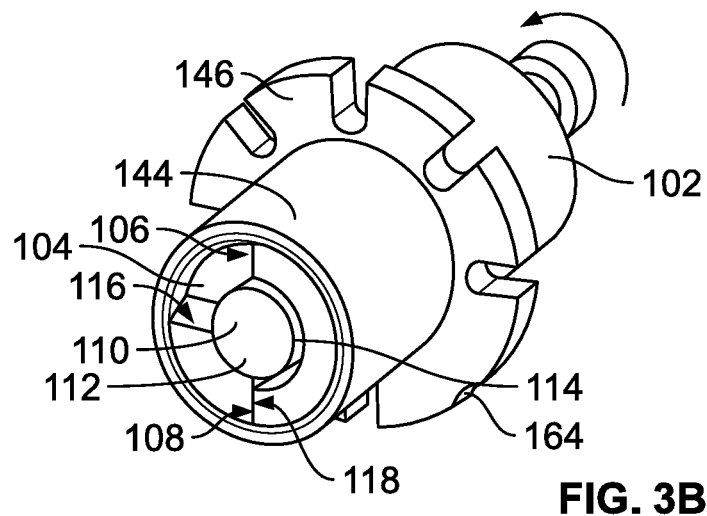
FIG. 3B is a perspective view of the insertion hub and retraction hub depicted in FIG. 3A in an inserted position.
Figure 3C:
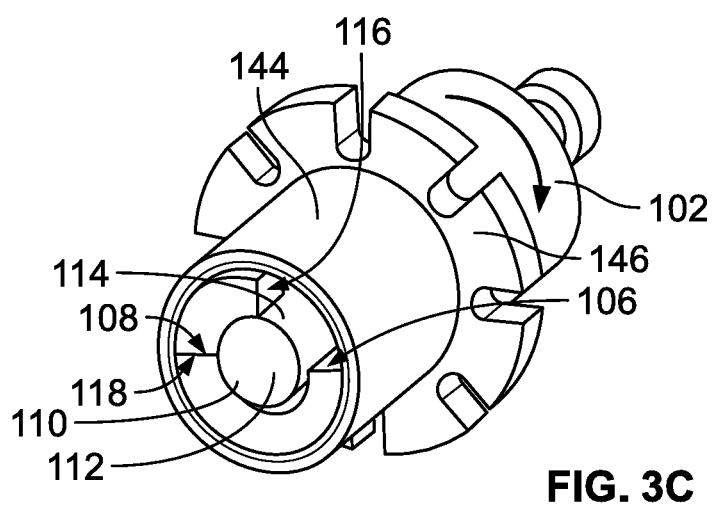
FIG. 3C is a perspective view of the insertion hub and retraction hub depicted in FIGS. 3A and 3B in a retracted position.

Turning to FIGS. 3A-3C, the interaction between the retraction hub 102 and the insertion hub 110 is better depicted. The retraction hub 102 comprises an inside surface 104. A first primary rotational stop 106 and a second primary rotational stop 108 extend radially inwardly from the inside surface 104. The insertion hub 110 is disposed inside of the retraction hub 102. The insertion hub 110 comprises a shaft 112 having an outside surface 114 with a first complementary rotational stop 116 and a second complementary rotational stop 118 extending radially outwardly from the outside surface 114. The shaft 112 connects to the spindle 120 of the insertion hub 120. As discussed in greater detail below, the first primary rotational stop 106 selectively engages the first complementary rotational stop 116 and the second primary rotational stop 108 selectively engages the second complementary rotational stop 118.

Figure 4A:
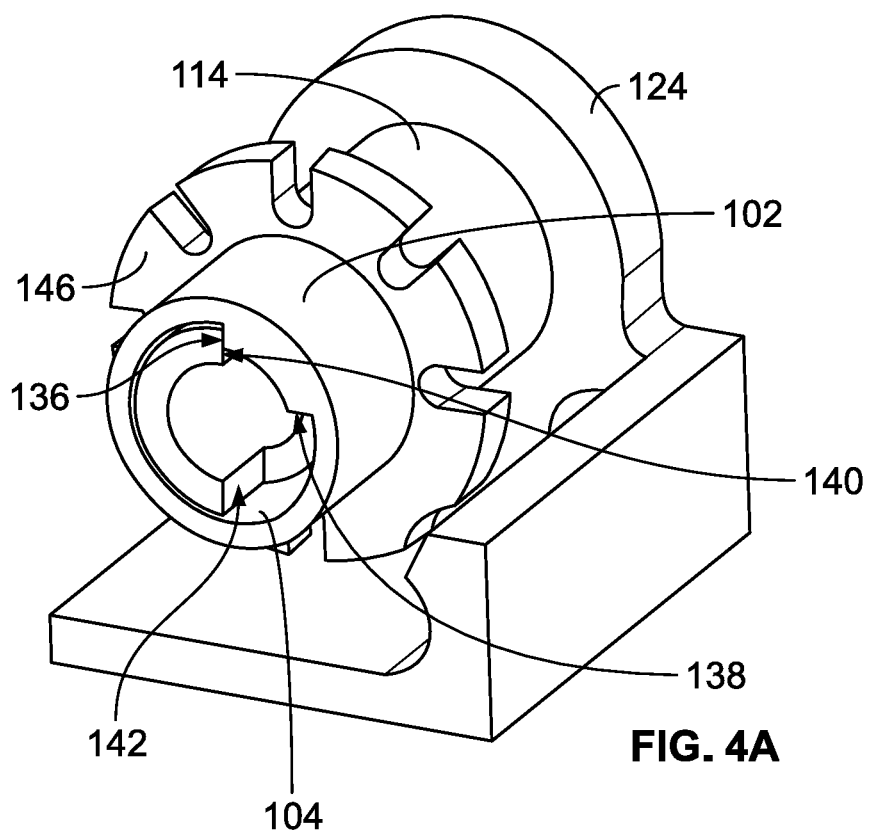
FIG. 4A is a perspective view of the retraction hub and insertion/retraction mechanism housing depicted in FIGS. 2A-2C in an initial position.
Figure 4B:
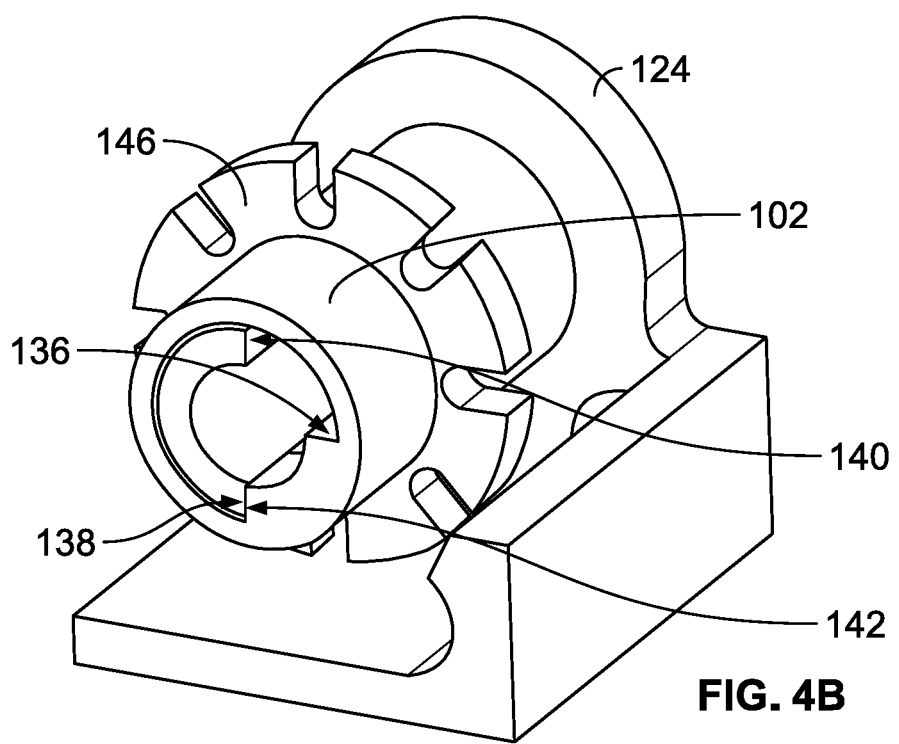
FIG. 4B is a perspective view of the retraction hub and insertion/retraction mechanism housing depicted in FIG. 4A in an inserted position.

Turning to FIGS. 4A-4B, the interaction between the retraction hub 102 and the insertion/retraction mechanism housing 124 is better depicted. The retraction hub 102 further comprises a third primary rotational stop 136 and a fourth primary rotational stop 138 extending radially inwardly from the inside surface 104. The insertion/retraction mechanism housing 124 comprises a third complementary rotational stop 140 and a fourth complementary rotational stop 142. As discussed in greater detail below, the third primary rotational stop 136 selectively engages the third complementary rotational stop 140 and the fourth primary rotational stop 138 selectively engages the fourth complementary rotational stop 142.

The insertion/retraction mechanism 12 has at least three positions: an initial position, an inserted position, and a retracted position. FIGS. 2A, and 3A depict the insertion/retraction mechanism 12 in the initial position. As shown in FIG. 2A, in the initial position, the flexible needle 34 does not pass through the needle exit aperture 126 of the insertion/retraction mechanism housing 124 and the retraction hub 102 is in a first rotational position relative to the insertion mechanism housing 124. As shown in FIG. 3A, in the initial position, the first primary rotational stop 106 of the retraction hub 102 engages the first complementary rotational stop 116 of the insertion hub 110.

FIGS. 2B, 3B, and 4A depict the insertion/retraction mechanism 12 in the inserted position. As shown in FIG. 2B, in the inserted position, the flexible needle 34 passes through the needle exit aperture 126 of the insertion/retraction mechanism housing 124. The retraction hub 102 is still in a first rotational position relative to the insertion mechanism housing 124. As shown in FIG. 3B, the second primary rotational stop 108 engages the second complementary rotational stop 118 as a result of the insertion hub 110 being rotated relative to the retraction hub 102 by a first spring bias provided by the dual torsion spring system 128. As shown in FIG. 4A, in the inserted position, the third primary rotational stop 136 of the retraction hub 102 engages the third complementary rotational stop 140 of the insertion/retraction mechanism housing 124. The distance that the flexible needle 34 extends beyond the needle exit aperture 126 in the inserted position is determined by a diameter D (identified in FIG. 5) of the spindle 120 of the insertion hub 110 and the first spring bias. By choosing the proper diameter D and the proper first spring bias, the flexible needle 34 can be reliably inserted to a desired depth of penetration in a subdermal region of the patient such as at an intramuscular, subcutaneous, or intradermal depth.

FIGS. 2C, 3C, and 4B depict the insertion/retraction mechanism 12 in the retracted position. As shown in FIG. 2C, in the retracted position, the flexible needle 34 does not pass through the needle exit aperture 126 of the insertion/retraction mechanism housing 124. The retraction hub 102 is in a second rotational position relative to the insertion/retraction mechanism housing 124 as a result of the retraction hub 102 being rotated relative to the insertion/retraction mechanism housing 124 by a second spring bias provided by the dual torsion spring system 128. As shown in FIG. 3C, the second primary rotational stop 108 still engages the second complementary rotational stop 118. As shown in FIG. 4B, the fourth primary rotational stop 138 of the retraction hub 102 engages the fourth complementary rotational stop 142 of the insertion/retraction mechanism housing 124.

The activation trigger 134 may be mechanical, electromechanical, pneumatic, hydraulic, or any other triggering means known in the art. In FIGS. 2A-2C, the activation trigger 134 comprises a sliding rod 148 axially aligned with the retraction hub 102 and having an outside surface 150 of varying outer diameter in contact with a sliding rod notch 164 of the retraction hub 102 and a sliding rod notch 166 of the insertion hub 110 A first axial movement of the sliding rod 148 releases the sliding rod 148 from the sliding rod notch 166 of the insertion hub 110, allowing one of the right wound torsion spring 130 and the left wound torsion spring 132 to rotate the insertion hub 110 relative to the retraction hub 102 to achieve the inserted position. A second axial movement of the sliding rod 148 releases the sliding rod 148 from the sliding rod notch 164 of the retraction hub 102, allowing the other of the right wound torsion spring 130 and the left wound torsion spring 132 to rotate the retraction hub 102 relative to the insertion/retraction mechanism housing 124 in order to achieve the retracted position.

Figure 5:
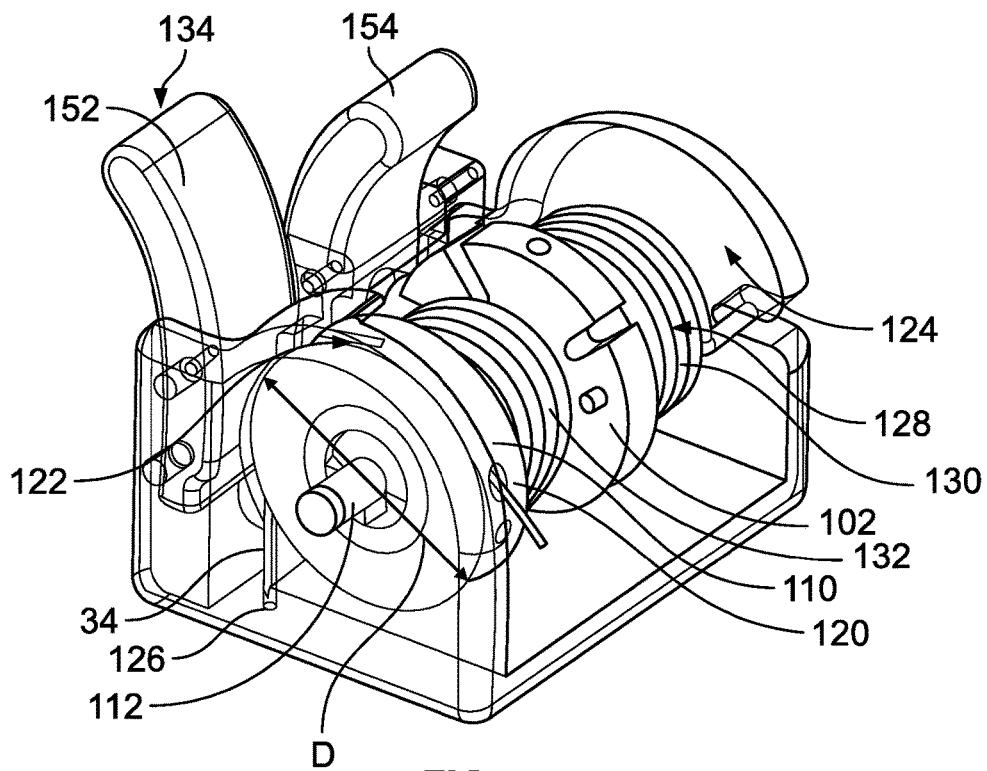
FIG. 5 is a perspective view of an arrangement of an insertion/retraction mechanism having a mechanical activation trigger including an insertion trigger selectively securing an insertion hub in place and a retraction trigger selectively securing a retraction hub in place in accordance with teachings of the present disclosure.

As shown in FIG. 5, the activation trigger 134 may include an insertion trigger 152 selectively securing the insertion hub 110 in place and a retraction trigger 154 selectively securing the retraction hub 102 in place. In such an arrangement, in the initial position, the insertion trigger 152 secures the insertion hub 110 in place and the retraction trigger 154 secures the retraction hub 102 in place. In the inserted position, the insertion trigger 152 does not secure the insertion hub 110 in place and the retraction trigger 154 still secures the retraction hub 102 in place. In the retracted position, the insertion trigger 152 does not secure the insertion hub 110 in place and the retraction trigger 154 does not secure the retraction hub 102 in place.

Figure 6:
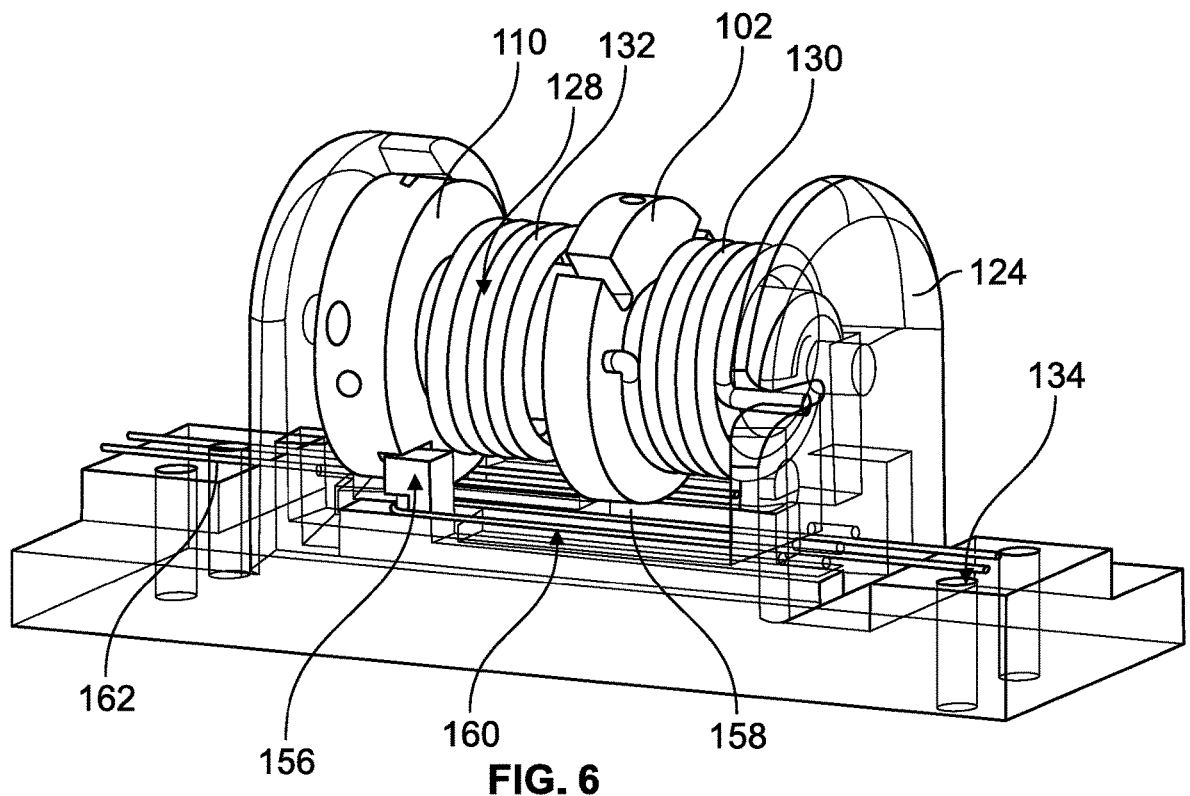
FIG. 6 is a perspective view of an arrangement of an insertion/retraction mechanism having an electrical activation trigger in accordance with teachings of the present disclosure.

As shown in FIG. 6, the activation trigger 134 may include a first sliding trigger 156 selectively securing one of the retraction hub 102 or the insertion hub 110 in place, a second sliding trigger 158 selectively securing the other of the retraction hub 102 or the insertion hub 110 in place, a first muscle wire 160 connected to the first sliding trigger 156, and a second muscle wire 162 connected to the second sliding trigger 158. Electrical activation of the first muscle wire 160 causes the first muscle wire 160 to contract, moving the first sliding trigger 158 and thereby releasing the one of the retraction hub 102 or the insertion hub 110, in order to allow one of the right wound torsion spring 130 and the left wound torsion spring 132 to rotate the insertion hub 110 relative to the retraction hub 102 to achieve the inserted position. Electrical activation of the second muscle wire 162 causes the second muscle wire 162 to contract, moving the second sliding trigger 158 and thereby releasing the other of the retraction hub 102 or the insertion hub 110, in order to allow the other of the right wound torsion spring 130 and the left wound torsion spring 132 to rotate the retraction hub 102 relative to the insertion/retraction housing 124 in order to achieve the retracted position.

In view of the foregoing, one of ordinary skill in the art will appreciate the following example method of inserting a flexible needle 34 of the needle insertion/retraction mechanism 12 for the drug delivery device 10 into a patient's skin.

The method includes, in an initial position, in which the flexible needle 34 of the insertion/retraction mechanism 12 is contained within the insertion/retraction mechanism housing 124, engaging the first primary rotational stop 106 of the retraction hub 102 with the first complementary rotational stop 116 of an insertion hub 110 and placing the retraction hub 102 in a first rotational position relative to the insertion/retraction mechanism housing 124. The method further includes triggering the activating trigger 134 operably connected to the dual torsion spring system 128 to cause one of the right wound torsion spring 130 and the left wound torsion spring 132 of the dual torsion spring system 128 to rotate the insertion hub 110 relative to the retraction hub 102 to achieve an inserted position where the second primary rotational stop 108 of the retraction hub 102 engages a second complementary rotational stop 118 of the insertion hub 110, the retraction hub 102 is in the first rotational position relative to the insertion/retraction mechanism housing 124, and the flexible needle 34 extends outside the insertion/retraction mechanism housing 124. The method further includes triggering the activation trigger 134 operably connected to the dual torsion spring system 128 to cause the other of the right wound torsion spring 130 and the left wound torsion spring 132 of the dual torsion spring system 128 to rotate the retraction hub 102 relative to the insertion/retraction mechanism housing 124 to achieve a retracted position in which the second primary rotational stop 108 of the retraction hub 102 engages the second complementary rotational stop 118 of the insertion hub 110, the retraction hub 102 is in a second rotational position relative to the insertion/retraction mechanism housing 124, and the flexible needle 34 is contained within the insertion/retraction mechanism housing 124.

In one example, used in conjunction with an injection/retraction mechanism 12 such as that depicted in FIG. 5, the method includes triggering the activation trigger 134 to achieve an inserted position by moving an insertion trigger 152 of the activation trigger 134 so that the insertion trigger 152 is not in contact with the insertion hub 110 while a retraction trigger 154 of the activation trigger 134 is in contact with the retraction hub 102. The method further includes triggering the activation trigger 134 to achieve a retracted position by moving the retraction trigger 154 so that the reaction trigger 154 is not in contact with the retraction hub 102.

In another example, used in conjunction with an injection/retraction mechanism 12 such as that depicted in FIGS. 2A-2C, the method includes triggering the activation trigger 134 to achieve an inserted position via a first axial movement of the sliding rod 148 axially aligned with the retraction hub 102 and the insertion hub 110 and having an outside surface 150 of varying outer diameter in contact with sliding rod notch 164 of the retraction hub 102 and sliding rod notch 166 of the insertion hub 110. The method further includes triggering the activation trigger 134 to achieve a retracted position via a second axial movement of the sliding rod 148.

In yet another example, used in conjunction with an injection/retraction mechanism 12 such as that depicted in FIG. 6, the method includes triggering the activation trigger 134 to achieve an inserted position via electrical activation of the first muscle wire 160 connected to the first sliding trigger 156 selectively securing one of the retraction hub 102 or the insertion hub 110 in place, thereby causing the first muscle wire 160 to contract, moving the first sliding trigger 156, and releasing the one of the retraction hub 102 or the insertion hub 110. The method further includes triggering the activation trigger 134 to achieve a retracted position via electrical activation of the second muscle wire 162 connected to the second sliding trigger 158 selectively securing the other of the retraction hub 102 or the insertion hub 110 in place, thereby causing the second muscle wire 162 to contract, moving the second sliding trigger 158, and releasing the other of the retraction hub 102 or the insertion hub 110.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof: OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003)

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the 0X40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti- CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNa mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the devices, systems, methods, and their elements.

What is claimed is:
1. A wearable drug delivery device comprising:
   a main housing having a container, a fluid pathway connector coupled to the container, and a pressure supply device; and
   an insertion/retraction mechanism disposed within the main housing and operatively coupled to the pressure supply device, the fluid pathway connector defining a fluid flow path between the container and the insertion/retraction mechanism, the insertion/retraction mechanism including:
   a retraction hub comprising an inside surface, a first primary rotational stop extending radially inwardly from the inside surface, and a second primary rotational stop extending radially inwardly from the inside surface;
   an insertion hub disposed inside of the retraction hub comprising a shaft having an outside surface, a first complementary rotational stop extending radially outwardly from the outside surface, and a second complementary rotational stop extending radially outwardly from the outside surface, the insertion hub further comprising a spindle connected to the shaft, the spindle having a needle pathway;
   an insertion/retraction mechanism housing that houses the retraction hub and the insertion hub in a rotatable manner and comprises a needle exit aperture;

a flexible needle connected to the fluid flow path and configured to extend through the needle pathway of the spindle of the insertion hub and to selectively pass through the needle exit aperture of the insertion/retraction mechanism housing during insertion and retraction of the flexible needle;

a dual torsion spring system, the dual torsion spring system, including a right wound torsion spring and a left wound torsion spring, operably connected to the retraction hub, the insertion hub, and the insertion/retraction mechanism housing; and an activation trigger operably connected to the dual torsion spring system;

wherein, in an initial position, the first primary rotational stop engages the first complementary rotational stop, the retraction hub is in a first rotational position relative to the insertion/retraction mechanism housing, and the flexible needle does not pass through the needle exit aperture, wherein, in an inserted position, the second primary rotational stop engages the second complementary rotational stop as a result of the insertion hub being rotated relative to the retraction hub by a first spring bias provided by the dual torsion spring system, the retraction hub is in the first rotational position relative to the insertion/retraction mechanism housing, and the flexible needle passes through the needle exit aperture, and wherein, in a retracted position, the second primary rotational stop engages the second complementary rotational stop, the retraction hub is in a second rotational position relative to the insertion/retraction mechanism housing as a result of the retraction hub being rotated relative to the insertion/retraction mechanism housing by a second spring bias provided by the dual torsion spring system, and the flexible needle does not pass through the needle exit aperture.

2. The wearable drug delivery device of claim 1,
wherein the retraction hub further comprises a third primary rotational stop extending radially inwardly from the inside surface and a fourth primary rotational stop extending radially inwardly from the inside surface,
wherein the insertion/retraction mechanism housing comprises a third complementary rotational stop and a fourth complementary rotational stop,
wherein the third primary rotational stop of the shaft of the insertion hub engages the third complementary rotational stop of the insertion/retraction mechanism housing in the inserted position, and
wherein the fourth primary rotational stop of the shaft of the insertion hub engages the fourth complementary rotational stop of the insertion/retraction mechanism housing in the retracted position.

3. The wearable drug delivery device of claim 1, wherein a distance that the flexible needle extends beyond the needle exit aperture in the inserted position is determined by a diameter of the insertion hub and the first spring bias.

4. The wearable drug delivery device of claim 1, wherein the right wound torsion spring and the left wound torsion spring are integrated together into a single two-stage torsion spring.

5. The wearable drug delivery device of claim 1,
wherein the retraction hub comprises an outside surface and preload notches extending radially outwardly from the outside surface,
and wherein one of the right wound torsion spring and the left wound torsion spring surrounds the outside surface of the retraction hub distal to the preload notches of the retraction hub and the other of the right wound torsion spring and the left wound torsion spring surrounds the outside surface of the retraction hub proximal to the preload notches of the retraction hub.

6. The wearable drug delivery device of claim 1,
wherein the retraction hub comprises an outside surface and a sliding rod notch extending radially outwardly from the outside surface,
wherein the insertion hub comprises a sliding rod notch extending radially outwardly from the outside surface,
wherein the activation trigger comprises a sliding rod axially aligned with the retraction hub and the insertion hub and having an outside surface of varying outer diameter in contact with the sliding rod notch of the retraction hub and the sliding rod notch of the insertion hub,
wherein a first axial movement of the sliding rod releases the sliding rod from the sliding rod notch of the insertion hub, allowing one of the right wound torsion spring and the left wound torsion spring to rotate the insertion hub relative to the retraction hub to achieve the inserted position, and
wherein a second axial movement of the sliding rod releases the sliding rod from the sliding rod notch of the retraction hub, allowing the other of the right wound torsion spring and the left wound torsion spring to rotate the retraction hub relative to the insertion/retraction mechanism housing in order to achieve the retracted position.

7. The wearable drug delivery device of claim 1,
wherein the activation trigger includes an insertion trigger selectively securing the insertion hub in place and a retraction trigger selectively securing the retraction hub in place,
wherein, in the initial position, the insertion trigger secures the insertion hub in place and the retraction trigger secures the retraction hub in place,
wherein, in the inserted position, the insertion trigger does not secure the insertion hub in place and the retraction trigger secures the retraction hub in place, and
wherein, in the retracted position, the insertion trigger does not secure the insertion hub in place and the retraction trigger does not secure the retraction hub in place.

8. The wearable drug delivery device of claim 1,
wherein the activation trigger comprises a first sliding trigger selectively securing one of the retraction hub or the insertion hub in place, a second sliding trigger selectively securing the other of the retraction hub or the insertion hub in place, a first muscle wire connected to the first sliding trigger, and a second muscle wire connected to the second sliding trigger, and
wherein electrical activation of the first muscle wire causes the first muscle wire to contract, moving the first sliding trigger and thereby releasing the one of the retraction hub or the insertion hub, in order to allow one of the right wound torsion spring and the left wound torsion spring to rotate the insertion hub relative to the retraction hub to achieve the inserted position;
wherein electrical activation of the second muscle wire causes the second muscle wire to contract, moving the second sliding trigger and thereby releasing the other of the retraction hub or the insertion hub, in order to allow the other of the right wound torsion spring and the left wound torsion spring to rotate the retraction hub relative to the insertion/retraction mechanism housing in order to achieve the retracted position.

9. An insertion/retraction mechanism for a drug delivery device, the insertion/retraction mechanism comprising:
a retraction hub comprising an inside surface, a first primary rotational stop extending radially inwardly from the inside surface, and a second primary rotational stop extending radially inwardly from the inside surface;
an insertion hub disposed inside of the retraction hub comprising a shaft having an outside surface, a first complementary rotational stop extending radially outwardly from the outside surface, and a second complementary rotational stop extending radially outwardly from the outside surface, the insertion hub further comprising a spindle connected to the shaft, the spindle having a needle pathway;
an insertion/retraction mechanism housing that houses the retraction hub and the insertion hub in a rotatable manner and comprises a needle exit aperture;
a flexible needle configured to extend through the needle pathway of the spindle of the insertion hub and to selectively pass through the needle exit aperture of the insertion/retraction mechanism housing during insertion and retraction of the flexible needle;
a dual torsion spring system, the dual torsion spring system, including a right wound torsion spring and a left wound torsion spring, operably connected to the retraction hub, the insertion hub, and the insertion/retraction mechanism housing; and
an activation trigger operably connected to the dual torsion spring system;
wherein, in an initial position, the first primary rotational stop engages the first complementary rotational stop, the retraction hub is in a first rotational position relative to the insertion/retraction mechanism housing, and the flexible needle does not pass through the needle exit aperture,
wherein, in an inserted position, the second primary rotational stop engages the second complementary rotational stop as a result of the insertion hub being rotated relative to the retraction hub by a first spring bias provided by the dual torsion spring system, the retraction hub is in the first rotational position relative to the insertion/retraction mechanism housing, and the flexible needle passes through the needle exit aperture, and
wherein, in a retracted position, the second primary rotational stop engages the second complementary rotational stop, the retraction hub is in a second rotational position relative to the insertion/retraction mechanism housing as a result of the retraction hub being rotated relative to the insertion/retraction mechanism housing by a second spring bias provided by the dual torsion spring system, and the flexible needle does not pass through the needle exit aperture.

10. The insertion/retraction mechanism of claim 9,
wherein the retraction hub further comprises a third primary rotational stop extending radially inwardly from the inside surface and a fourth primary rotational stop extending radially inwardly from the inside surface,
wherein the insertion/retraction mechanism housing comprises a third complementary rotational stop and a fourth complementary rotational stop,
wherein the third primary rotational stop of the shaft of the insertion hub engages the third complementary rotational stop of the insertion/retraction mechanism housing in the inserted position, and
wherein the fourth primary rotational stop of the shaft of the insertion hub engages the fourth complementary rotational stop of the insertion/retraction mechanism housing in the retracted position.

11. The insertion/retraction mechanism of claim 9, wherein a distance that the flexible needle extends beyond the needle exit aperture in the inserted position is determined by a diameter of the insertion hub and the first spring bias.

12. The insertion/retraction mechanism of claim 9, wherein the right wound torsion spring and the left wound torsion spring are integrated together into a single two-stage torsion spring.

13. The insertion/retraction mechanism of claim 9,
wherein the retraction hub comprises an outside surface and preload notches extending radially outwardly from the outside surface,
and wherein one of the right wound torsion spring and the left wound torsion spring surrounds the outside surface of the retraction hub distal to the preload notches of the retraction hub and the other of the right wound torsion spring and the left wound torsion spring surrounds the outside surface of the retraction hub proximal to the preload notches of the retraction hub.

14. The insertion/retraction mechanism of claim 9,
wherein the retraction hub comprises an outside surface and a sliding rod notch extending radially outwardly from the outside surface,
wherein the insertion hub comprises a sliding rod notch extending radially outwardly from the outside surface,
wherein the activation trigger comprises a sliding rod axially aligned with the retraction hub and having an outside surface of varying outer diameter in contact with the sliding rod notch of the retraction hub and the sliding rod notch of the insertion hub,
wherein a first axial movement of the sliding rod releases the sliding rod from the sliding rod notch of the insertion hub, allowing one of the right wound torsion spring and the left wound torsion spring to rotate the insertion hub relative to the retraction hub to achieve the inserted position, and
wherein a second axial movement of the sliding rod releases the sliding rod from the sliding rod notch of the retraction hub, allowing the other of the right wound torsion spring and the left wound torsion spring to rotate the retraction hub relative to the insertion/retraction mechanism housing in order to achieve the retracted position.

15. The insertion/retraction mechanism of claim 9,
wherein the activation trigger includes an insertion trigger selectively securing the insertion hub in place and a retraction trigger selectively securing the retraction hub in place,
wherein, in the initial position, the insertion trigger secures the insertion hub in place and the retraction trigger secures the retraction hub in place,
wherein, in the inserted position, the insertion trigger does not secure the insertion hub in place and the retraction trigger secures the retraction hub in place, and
wherein, in the retracted position, the insertion trigger does not secure the insertion hub in place and the retraction trigger does not secure the retraction hub in place.

16. The insertion/retraction mechanism of claim 9,
wherein the activation trigger comprises a first sliding trigger selectively securing one of the retraction hub or the insertion hub in place, a second sliding trigger selectively securing the other of the retraction hub or the insertion hub in place, a first muscle wire connected to the first sliding trigger, and a second muscle wire connected to the second sliding trigger, and
wherein electrical activation of the first muscle wire causes the first muscle wire to contract, moving the first sliding trigger and thereby releasing the one of the retraction hub or the insertion hub, in order to allow one of the right wound torsion spring and the left wound torsion spring to rotate the insertion hub relative to the retraction hub to achieve the inserted position;
wherein electrical activation of the second muscle wire causes the second muscle wire to contract, moving the second sliding trigger and thereby releasing the other of the retraction hub or the insertion hub, in order to allow the other of the right wound torsion spring and the left wound torsion spring to rotate the retraction hub relative to the insertion/retraction mechanism housing in order to achieve the retracted position.

17. A method of deploying a needle of an insertion/retraction mechanism from a drug delivery device, the method comprising:
in an initial position, in which a flexible needle of the insertion/retraction mechanism is contained within an insertion/retraction mechanism housing, engaging a first primary rotational stop of a retraction hub with a first complementary rotational stop of an insertion hub and placing the retraction hub in a first rotational position relative to the insertion/retraction mechanism housing;
triggering an activation trigger operably connected to a dual torsion spring system to cause one of a right wound torsion spring and a left wound torsion spring of the dual torsion spring system to rotate the insertion hub relative to the retraction hub to achieve an inserted position where a second primary rotational stop of the retraction hub engages a second complementary rotational stop of the insertion hub, the retraction hub is in the first rotational position relative to the insertion/retraction mechanism housing, and the flexible needle extends outside the insertion/retraction mechanism housing;
triggering the activation trigger operably connected to the dual torsion spring system to cause the other of the right wound torsion spring and the left wound torsion spring of the dual torsion spring system to rotate the retraction hub relative to the insertion/retraction mechanism housing to achieve a retracted position in which the second primary rotational stop of the retraction hub engages the second complementary rotational stop of the insertion hub, the retraction hub is in a second rotational position relative to the insertion/retraction mechanism housing, and the flexible needle is contained within the insertion/retraction mechanism housing.

18. The method of deploying a needle of an insertion/retraction mechanism from a drug delivery device of claim 17, further comprising:
triggering the activation trigger to achieve an inserted position by moving an insertion trigger of the activation trigger so that the insertion trigger is not in contact with the insertion hub while a retraction trigger of the activation trigger is in contact with the retraction hub;
triggering the activation trigger to achieve a retracted position by moving the retraction trigger so that the reaction trigger is not in contact with the retraction hub.

19. The method of deploying a needle of an insertion/retraction mechanism from a drug delivery device of claim 17, further comprising:
triggering the activation trigger to achieve an inserted position via a first axial movement of a sliding rod axially aligned with a retraction hub and having an outside surface of varying outer diameter in contact with a sliding rod notch of the retraction hub and a sliding rod notch of the insertion hub; and
triggering the activation trigger to achieve a retracted position via a second axial movement of the sliding rod.

20. The method of deploying a needle of an insertion/retraction mechanism from a drug delivery device of claim 17, further comprising:
triggering the activation trigger to achieve an inserted position via electrical activation of a first muscle wire connected to a first sliding trigger selectively securing one of the retraction hub or the insertion hub in place, thereby causing the first muscle wire to contract, moving the first sliding trigger, and releasing the one of the retraction hub or the insertion hub;
triggering the activation trigger to achieve a retracted position via electrical activation of a second muscle wire connected to a second sliding trigger selectively securing the other of the retraction hub or the insertion hub in place, thereby causing the second muscle wire to contract, moving the second sliding trigger, and releasing the other of the retraction hub or the insertion hub.

* * * * *

UNITED STATES PATENT AND TRADEMARK OFFICE
CERTIFICATE OF CORRECTION

PATENT NO. : 11,305,056 B2
APPLICATION NO. : 16/620016
DATED : April 19, 2022
INVENTOR(S) : Mehran Mojarrad et al.

It is certified that error appears in the above-identified patent and that said Letters Patent is hereby corrected as shown below:

On the Title Page

At item (22), Line 1, "Jul. 14, 2018" should be -- Jul. 03, 2018 --.

Signed and Sealed this
Twentieth Day of December, 2022

Katherine Kelly Vidal
*Director of the United States Patent and Trademark Office*